US00PP29809P2

(12) United States Plant Patent
Lee

(10) Patent No.: US PP29,809 P2
(45) Date of Patent: Nov. 6, 2018

(54) **NEW GUINEA *IMPATIENS* PLANT NAMED 'IMGZ0012'**

(50) Latin Name: *Impatiens hawkeri*
Varietal Denomination: IMGZ0012

(71) Applicant: SYNGENTA PARTICIPATIONS AG, Basel (CH)

(72) Inventor: Jaemin Lee, Gilroy, CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/732,235

(22) Filed: Oct. 10, 2017

(51) Int. Cl.
*A01H 5/02* (2018.01)

(52) U.S. Cl.
USPC ..... Plt./318.7

(58) Field of Classification Search
USPC ..... Plt./318.7
See application file for complete search history.

*Primary Examiner* — Annette H Para
(74) *Attorney, Agent, or Firm* — Dale Skalla

(57) ABSTRACT

A new New Guinea *Impatiens* plant named 'IMGZ00012' particularly distinguished by the dark red flower on short peduncles on a medium sized well branched plant with deep dark green foliage.

1 Drawing Sheet

Latin name of the genus and species of the plant claimed: *Impatiens hawkeri.*

Varietal denomination: 'IMGZ0012'.

BACKGROUND OF THE NEW PLANT

The present invention comprises a new New Guinea *Impatiens*, botanically known as *Impatiens hawkeri*, and hereinafter referred to by the variety name 'IMGZ0012'.

'IMGZ0012' is a product of a planned breeding program. The new cultivar has large, flat flowers with a relatively dark red pattern. The foliage is very deep dark green with light red veins on the upper and lower side of the leaf. The space between the leaf veins on the upper and lower side is reddish. The plant is medium sized and well branched.

'IMGZ0012' originated from a hybridization made in June 2010 in a controlled breeding environment in Enkhuizen, The Netherlands.

The female parent is designated as 'k05-0993-1' with magenta flower color. The male parent is designated as 'Q2460-1' and is large sized and has dark red flower pattern.

The resultant seed was sown in November 2011 in a greenhouse in Enkhuizen, The Netherlands and 'IMGZ0012' was selected there as one flowering plant within the progeny of the stated cross in spring 2012.

The first act of asexual reproduction of 'IMGZ0012' was accomplished when vegetative cuttings were propagated from the initial selection in June 2012 in a controlled environment in Moncarapacho, Portugal.

BRIEF SUMMARY OF INVENTION

Horticultural examination of plants grown from cuttings of the plant initiated in July 2017 in Gilroy, Calif. USA, has demonstrated that the combination of characteristics as herein disclosed for 'IMGZ0012' are firmly fixed and are retained through successive generations of asexual reproduction.

'IMGZ0012' has not been observed under all possible environmental conditions. The phenotype may vary significantly with variations in environment such as temperature and light intensity.

A Plant Breeder's Right for this cultivar has not yet been applied for. 'IMGZ0012' has not been made publicly available prior to the effective filing date of this application, notwithstanding any disclosure that may have been made less than one year prior to the effective filing date of this application by the inventor or another who obtained 'IMGZ0012' directly from the inventor.

The following traits have been repeatedly observed and are determined to be basic characteristics of the new variety. The combination of these characteristics distinguishes this *Impatiens* as a new and distinct variety.

BRIEF DESCRIPTION OF THE PHOTOGRAPHS

The accompanying photographic drawings show typical flower and foliage characteristics of 'IMGZ0012' with colors being as true as possible with an illustration of this type.

Figure 1:
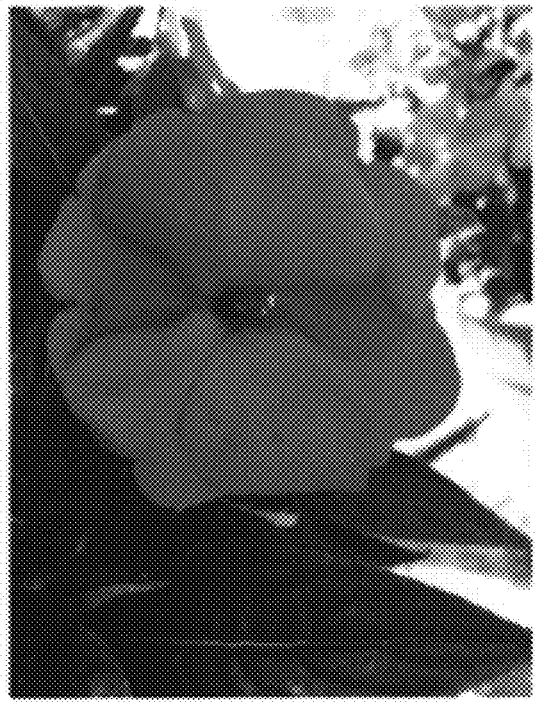
Figure 2:
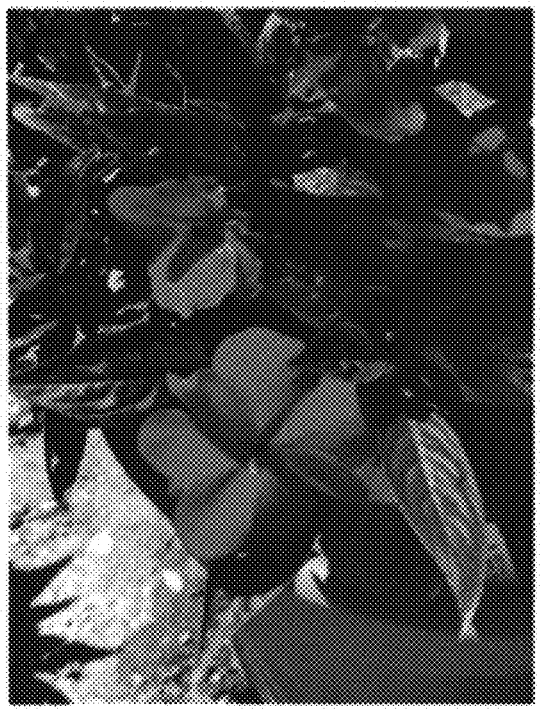

The photographic drawings show in FIG. 1 a close-up of the flowers and in FIG. 2 a flowering plant of the new variety growing in 14 cm pot.

DETAILED BOTANICAL DESCRIPTION

The aforementioned photographs were taken in July 2017 from plants grown in a container trial in Gilroy, Calif. USA. These plants were growing in 14 cm pots and were approximately 17 weeks of age.

The plant descriptions and measurements were taken in May, 2017, on 17-week old plants growing in a greenhouse in Gilroy, Calif. USA. Cuttings were stuck in week 13 for rooting, planted into 10 cm pots in week 18, and were grown, without pinching, on benches in a greenhouse, initially at a day temperature of 18° C. and night temperature of 16° C. However, day temperatures often raised above 20° C.

Color references are made to The Royal Horticultural Society Colour Chart (R.H.S.) 2001.

TABLE 1

DIFFERENCES BETWEEN THE NEW VARIETY 'IMGZ0012' AND SIMILAR PATENTED VARIETIES

| | 'IMGZ0012' | 'NG089' ('Sonic Red') | 'NG072' ('Sonic Deep Red') |
|---|---|---|---|
| Flower color: | Dark red | Red | Deep red |
| Flower pattern: | Sharp | Very sharp | Not sharp |
| Habit/vigor: | Medium | Medium | Small |
| Branching: | Better | Less | Less |

Plant:

*Form, growth and habit.*—Medium sized, up-mounded, well branched.

*Plant height.*—21.0 cm (without pot), 33 cm (with pot).

*Plant height (inflorescence included).*—20.0-22.0 cm (without pot).

*Plant width.*—27.0 cm

Roots:

*Number of days to initiate roots.*—7 days at about 22 degrees C.

*Number of days to produce a rooted cutting.*—15-18 days at 22 degrees C.

*Type.*—Fibrous, free branching.

*Color.*—RHS 159A.

Foliage:

*Arrangement.*—Simple leaves, mainly in whorls.

*Young leaf, color upper surface.*—RHS 147A.

*Young leaf, color lower surface.*—Closest RHS 147C.

*Mature leaf, color upper surface.*—RHS 147A.

*Mature leaf, color lower surface.*—Closest to RHS 147B.

*Length.*—Up to 13 cm.

*Width.*—Up to 5 cm.

*Shape.*—Lanceolate.

*Base shape.*—Lanceolate.

*Apex shape.*—Acuminate.

*Margin.*—Serrulate, with short bristles.

*Texture.*—Slightly waxy and glossy on the upper surface, glabrous on both surfaces.

*Color of veins, upper surface.*—RHS 147C.

*Color of veins, lower surface.*—RHS 183D.

*Petiole color, upper side.*—RHS 183C.

*Petiole color, lower side.*—RHS 183B.

*Length.*—Up to 5.5 cm.

*Diameter.*—0.1 cm.

*Texture.*—Glabrous.

Stem:

*Color of stem.*—RHS 183B.

*Length of stem.*—About 14.5 cm.

*Diameter.*—2 cm.

*Length of internodes.*—Approximately 2 to 6 cm.

*Texture.*—Smooth, glabrous.

*Number of branches.*—6 main branches plus 9 side branches per main branch.

*Color of peduncle.*—RHS 46A.

*Length of peduncle.*—2.4-3.0 cm.

*Peduncle diameter.*—0.6 cm.

*Texture.*—Glabrous.

Inflorescence:

*Blooming habit.*—Continuous flowering from late spring through fall.

*Type of inflorescence.*—Solitary flowers emerge from the upper leaf nodes of the stem.

*Number of flowers per node.*—1-3 open flowers and additional buds in various stages of development.

*Quantity of flowers per plant.*—2 open flowers plus 20 (big and small) buds (8.5 cm pot plant in October).

*Lastingness of individual blooms on the plant.*—About 6-9 days.

*Fragrance.*—None.

Bud (just before opening):

*Color.*—RHS 183B.

*Length.*—Up to 2.6 cm.

*Width.*—Up to 2 cm.

*Shape.*—Ovate.

Immature flowers:

*Color of petals, upper surface.*—RHS N30A+RHS 75B.

*Color of petals, lower surface.*—RHS 39B.

Mature flowers:

*Flower, vertical length.*—6.5 cm.

*Flower, horizontal width.*—6.7 cm.

*Flower depth.*—1.5-2.0 cm.

*Color of petals, upper surface.*—RHS 46A.

*Color of petals, lower surface.*—RHS 46C.

*Petal shape.*—Heart shaped.

*Petal apex shape.*—Broadly obcordate.

*Petal margin.*—Entire.

*Petal texture, upper surface.*—Papillose.

*Petal texture, lower surface.*—Papillose.

Calyx:

*Arrangement.*—One large sepal bearing the spur, 2 small, lateral sepals, and 1 fused keel.

Large sepal(s):

*Color, visible surface.*—RHS 50C to RHS 50A.

*Length.*—1.9 cm.

*Width.*—1.4 cm.

*Shape.*—Ovate.

*Apex shape.*—Aristate.

*Base.*—Fused with the spur.

*Margins.*—Entire.

*Texture, upper surface.*—Papillose.

*Texture, lower surface.*—Papillose.

Lateral sepals:

*Color of surface.*—RHS 166A.

*Length.*—1.3 cm.

*Width.*—0.6-0.7 cm.

*Shape.*—Ovate.

*Apex shape.*—Acuminate.

*Base.*—Fused.

*Margins.*—Entire.

*Texture, upper surface.*—Glabrous.

*Texture, lower surface.*—Glabrous.

*Keel color.*—From RHS 46A to more brownish tones, closest to RHS 185A.

Spur:

*Color.*—RHS 144C.

*Length.*—4.5-4.8 cm.

*Diameter.*—0.3 cm at the base, 0.1 cm at tip.

Reproductive organs:

Androecium: 5 stamen, fused with the anthers hooded.

*Diameter of androeceum.*—0.7 cm.

*Surface color.*—RHS N57B, fading towards margin.

*Pollen amount.*—Plenty.

*Color of pollen.*—RHS 8D.

Gynoecium:

*Pistil*.—One, elongate.

*Pistil length*.—0.6 cm.

*Stigma color*.—RHS N57B.

*Ovary color*.—Dark brown, RHS 183A to RHS 144B. (green).

*Fertility/seed set*.—Has not been observed on this hybrid.

*Disease/pest resistance*.—Has not been observed on this hybrid. However, it is known for *Impatiens* New Guinea that it is downy mildew resistant.

What is claimed is:

1. A new and distinct variety of New Guinea *Impatiens* plant named 'IMGZ0012' substantially as illustrated and described herein.

* * * * *